United States Patent [19]

Dozzi et al.

[11] 4,193,939

[45] Mar. 18, 1980

[54] PROCESS FOR THE SYNTHESIS OF MIXED POLYIMINO DERIVATIVES OF ALUMINUM AND ALKALINE EARTH METALS

[75] Inventors: Giovanni Dozzi, Milan; Salvatore Cucinella; Alessandro Mazzei, both of San Donato Milanese, all of Italy

[73] Assignee: Anic S.p.A., Palermo, Italy

[21] Appl. No.: 678

[22] Filed: Jan. 3, 1979

Related U.S. Application Data

[62] Division of Ser. No. 831,240, Sep. 7, 1977.

[30] Foreign Application Priority Data

Oct. 28, 1976 [IT] Italy .............................. 28776 A/76
Oct. 28, 1976 [IT] Italy .............................. 28777 A/76

[51] Int. Cl.$^2$ ............................................. C07C 83/00
[52] U.S. Cl. ................................................. 260/583 R
[58] Field of Search ..................................... 260/583 R

[56] References Cited

U.S. PATENT DOCUMENTS

| | | | |
|---|---|---|---|
| 2,141,058 | 12/1938 | Liegler ............................. | 260/583 R |
| 2,685,604 | 8/1954 | Humphreys ..................... | 260/583 R |
| 2,750,417 | 6/1956 | Closson et al. ............... | 260/583 R X |
| 3,542,512 | 11/1970 | Honeycutt ....................... | 260/583 R |
| 3,917,062 | 11/1975 | Normant ......................... | 260/583 R |

OTHER PUBLICATIONS

Smith, The Chemistry of Open-Chain Org. Nitrogen Compounds, W. A. Benjamin, Inc. N.Y. p. 92 (1965).
Heuben-Weyl Methoden der Organischen Chemie, Band X1/2 (1958), pp. 182–187.

*Primary Examiner*—Helen M. S. Sneed
*Attorney, Agent, or Firm*—Morgan, Finnegan, Pine, Foley & Lee

[57] ABSTRACT

A single stage process is provided for the direct synthesis of mixed polyimino derivatives of aluminum and alkaline earth metals consisting of reacting aluminum, an amine, the alkaline earth metal or hydride or amide derivative thereof, in the presence of hydrogen, the reaction being promoted by an activator in either hydrocarbon or ether solvents.

3 Claims, No Drawings

PROCESS FOR THE SYNTHESIS OF MIXED POLYIMINO DERIVATIVES OF ALUMINUM AND ALKALINE EARTH METALS

This is a division, of application Ser. No. 831,240 filed Sept. 7, 1977.

This invention relates to a process for the direct synthesis of mixed polyimino derivatives of aluminium and alkaline earth metals starting from the metals or derivatives of the metals concerned.

The invention also relates to the synthesis of certain compounds suitable for carrying out said process. Mixed polyimino derivatives may be considered to be derived from poly(N-alkyliminoalanes) of composition $$(\text{HAlNR})_n \tag{I}$$

$$[(\text{HAlNR})_m(\text{H}_2\text{AlNHR})_n] \tag{II}$$

in which R is a hydrocarbon radical, n is a whole number less than or equal to 10, m is a number such that the sum of m+n is still a whole number less than or equal to 10, and in which one or more —AlH— groups are replaced by atoms of alkaline earth metals.

The resultant compounds are of composition $$[(\text{HAlNR})_a(\text{MNR})_b] \tag{III}$$

in which:
(1) b≠o
(2) a+b may vary between 4 and 20
(3) a=b, or a≠b, and more generally a>b,
and of composition $$[(\text{HAlNR})_a(\text{H}_2\text{AlNHR})_b(\text{MNR})_c(\text{HMNR})_d] \tag{IV}$$

in which:
(1) (c+d)≠o
(2) (a+b+c+d) may vary between 2 and 20
(3) (a+b)=(c+d), or (a+b)≠(c+d), and more generally (a+b)>(c+d). Compounds of class (III) fall within the more general class (IV) when b=d=0.

In certain previous Italian patents, the same applicant has described the synthesis of compounds both of formula (III) and formula (IV) starting from the alanate of the alkaline earth metal, for example in accordance with reactions 1, 2 or 3, or from amides of alkaline earth metals in accordance with reaction 4.

$$x\text{M(AlH}_4)_2 + 3x\text{RNH}_2 \rightarrow \ldots$$
$$1/x[(\text{MNR})(\text{HAlNR})_2]_x \ldots + 6x\text{H}_2 \tag{1}$$

$$x\text{M(AlH}_4)_2 + 3x\text{RCN} \rightarrow \ldots$$
$$1/x[(\text{MNR'})(\text{HAlNR'})_2]_x \ldots \tag{2}$$

$$\text{M(AlH}_4)_2 + \text{AlH}_3 + 4\text{RNH}_2 \rightarrow [(\text{MNR})(\text{HAlNR})_3] + 8\text{H}_2 \tag{3}$$

$$2\text{Mg(NHR)}_2 + 2\text{AlH}_3 \rightarrow 1/n[(\text{MgNR})(\text{HAlNR})_2]_n + 1/m\,(\text{MgNR})_m + 4\text{H}_2 \tag{4}$$

All these methods comprise:
1. The use of hydride derivatives of aluminium which have been previously synthesised, often by complicated methods.

In particular, reactions 1 and 2 require the use of M(AlH$_4$)$_2$ which is obtained for example in the case of Mg by reaction 5

$$\text{MgI}_2 + 2\text{LiAlH}_4 \rightarrow \text{Mg(AlH}_4)_2 + 2\text{LiI}_2 \tag{5}$$

and in the case of Ca, by reaction 6

$$4\text{CaH}_2 + 2\text{AlCl}_3 \rightarrow \text{Ca(AlH}_4)_2 + 3\text{CaCl}_2 \tag{6}$$

Both the reactions 5 and 6 include the formation of metal halides as by-products, with consequent problems of filtration, loss of costly metals etc.

Reaction 3 also requires the use of complexes of AlH$_3$ with Lewis bases. Of these, only the complex with triethylenediamine is obtainable by direct synthesis from Al, H$_2$ and amine (E. C. Ashby J. Am. Chem. Soc. 86 1882 (1964)).

On the other hand, the synthesis of complexes with diethyl ether, tetrahydrofuran, trimethylamine etc., which are more commonly used, is obtained by reaction 7, which has drawbacks similar to reactions 5 and 6.

$$3\text{MAlH}_4 + \text{AlCl}_3 \rightarrow 4\text{AlH}_3 + 3\text{MCl} \tag{7}$$

M=Li or Na

Reaction 4 uses alkaline earth metal amides obtainable, according to our previous patent application, by direct synthesis from Mg and amine in the presence of H$_2$.

If AlH$_3$.N(CH$_2$.CH$_2$)$_3$N were used, synthesised from its elements in accordance with the aforementioned method of E. C. Ashby, reaction 4 would require the use of a synthesis process under high H$_2$ pressure using different methods for each of the two reactants.

2. Furthermore, each of reactions 1 to 4 gives rise to the loss of hydride hydrogen.

We have now discovered a single stage method for preparing mixed polyimino derivatives of aluminium and alkaline earth metals of formula (III) and (IV) starting from the metals and amine in the presence of H$_2$ in accordance with general reaction 8

$$x\text{M} + y\text{Al} + s\text{RNH}_2 \rightarrow [(\text{HAlNR})_a(\text{H}_2\text{AlNHR})_b(\text{MNR})_c(\text{HMNR})_d] + k\text{H}_2 \tag{8}$$

in which:

M=alkaline earth metal (a+b)=y; (c+d)=x; x+y=z;
k=(x+y/2)−½(b+d)

Instead of M, the hydride MH$_2$ may be used as the starting material in accordance with reaction 9

$$x\text{MH}_2 + y\text{Al} + z\text{RNH}_2 \rightarrow [(\text{HAlNR})_a(\text{H}_2\text{AlNHR})_b(\text{MNR})_c(\text{HMNR})_d] + k\text{H}_2 \tag{9}$$

in which
M=alkaline earth metal (a+b)=y; (c+d)=x; x+y=z;
k=(2x+y/2)−½(b+d)

As an alternative, the alkaline earth metal M or its hydride MH$_2$ may be replaced as starting material by one of its amido derivatives.

In the special case of magnesium, the applicant has also discovered a new method for the synthesis of the corresponding amide derivatives. The details of this method, which constitutes an integral part of the present invention, will be given hereinafter. The composition of these products is such that the atomic ratio N/M may be equal to or less than 2.

Their use as starting material leads to a reduction in the amine quantity relative to that used in reaction 8, equal to the quantity bonded to the alkaline earth metal.

This is exemplified in reaction 10, which for example uses amides of composition M(NHR)$_2$:

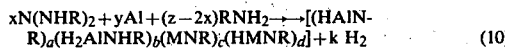   (10)

In all cases the loss of hydride hydrogen and the formation of unusable by-products are avoided. Reactions 8, 9 and 10 or the aforesaid modifications thereof are conducted in a hydrocarbon or ether solvent under a hydrogen pressure variable between 5 and 1000 kg/cm$^2$ and at a temperature variable between 30° C. and the decomposition temperature of the product in the presence of an activator.

The preferred conditions are a temperature of 100° to 200° C. according to the physical-chemical characteristics of the solvent, and a hydrogen pressure of 100 to 250 kg/cm$^2$.

The reactions are accelerated by the presence of an activator, the molar quantity of which need only be equal to or less than 5% of the amine and is chosen from alkaline metals, their derivatives, alkyl aluminium or alane complexes with Lewis bases.

If the reactions are conducted in an ether solvent, for example tetrahydrofuran, solvent molecules result at the end in complex with the alkaline earth metal atoms in the final reaction product. As stated heretofore, the present invention also relates to a process for preparing magnesium amides, by direct reaction of magnesium and amine.

These products, of formula RMg(NR'$_2$) and Mg(NR$_2$)$_2$, in which R and R', which are the same or different, are hydrocarbon radicals of various types, have up to the present time been synthesised from organic magnesium derivatives of formula MgR$_2$, these latter being obtainable only from Grignard compounds. This fact bears heavily on the magnesium amide preparation process, which thus becomes too complicated, as shown by the following equations:

   (1)

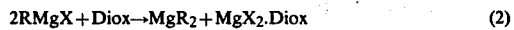   (2)

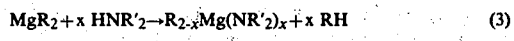   (3)

X=halogen
Diox=dioxan
x=1 or 2

We have now discovered that it is possible to synthesise magnesium amides from magnesium metal, by direct reaction with primary or secondary amines.

The reaction takes place in the presence of H$_2$ and is promoted by an activator, in either hydrocarbon or ether solvents.

The reaction temperature varies over a wide range, the preferred temperature varying from 50° to 150° C. for reactions in ether solvents, and higher for reactions in hydrocarbon solvents.

Various activators promote the reaction, and are chosen from metals of the first three groups of the periodic table, their hydrides or alkyl derivatives, or mixed hydrides thereof.

Relatively small quantities may be used, generally equal to or less than 5 molar % of the reacted amine. Examples of activators are Na, NaH, NaAlH$_4$, AlEt$_3$, AlH$_3$.B, MgH$_2$, MgR$_2$ etc.

In the case of secondary amines, the reaction products are of formula Mg(NR$_2$)$_2$.

Starting with primary amines, the composition and physical-chemical characteristics of the reaction product vary as the ratio of amine to magnesium reactants varies.

Generally by using an excess of amine it is possible to obtain products in which the atomic N/Mg ratio is equal to about 2, corresponding to the formation of Mg(NHR)$_2$ with a practically quantitative yield in terms of the magnesium if an adequate reaction temperature is ensured. In other cases, or if using an excess of Mg, reaction products are obtained having an atomic N/Mg ratio less than 2.

The importance of, and the need for a simple method for obtaining magnesium amides are evident from the numerous applications of these compounds.

Amongst others:
(a) magnesium amides may be used as polymerisation catalysts, for example in the case of methacrylonitrile;
(b) magnesium amides may be used in the amination of organic substrates, for example to obtain alkyl amides from organic acids, acid chlorides etc., Schifff bases from substrates containing carboxylic groups etc.;
(c) magnesium amides allow simple synthesis of polyiminoalanes, as heretofore described.

EXAMPLE 1

A suspension of powdered magnesium (150 mg. atoms), powdered aluminium (210 mg. atoms), sodium aluminium hydride (10 m moles) and tertiary butylamine (280 m moles) in tetrahydrofuran (400 ml) is fed in that order into a 1 liter stainless steel autoclave provided with a rotating agitator and evacuated of air.

It is pressurised to 140 kg/cm$^2$ at ambient temperature, and then heated to 100° C which the pressure increases to 190 kg/cm$^2$.

It is left in agitation under these conditions for 40 hours, then cooled, depressurized and the reaction mixture filtered.

The insoluble residue is repeatedly washed with small amounts of tetrahydrofuran and the solution resulting from the wash is combined with the mother liquid to give a total of 450 ml of solution, which on analysis shows:
Al=0.44 g. atoms/liter
Mg=0.145 g. atoms/liter
N=0.555 g. atoms/liter
H$_{act}$=0.396 meq/liter
from which the following atomic ratios are obtained
Mg/Al=0.33; N/Al=1.26; H$_{act}$/Al=0.9

When subjected to X-ray examination, the residual product from evaporating the solvent shows a crystallinity different from that which is characteristic of the simple tetra (N-tertiary butyliminoalane), which results from reacting Al with tertiary butylamine under a pressure of H$_2$ in the absence of Mg.

EXAMPLE 2

A solution of magnesium isopropylamide, in which the N/Mg ratio=1.5 (50 mg. atoms of Mg) in toluene (100 ml), and a mixture of powdered aluminium (100 mg. atoms), isopropylamine (70 m moles), and NaAlH$_4$ (5 m moles) in toluene (200 ml) are fed in that order into a 1 liter stainless steel autoclave provided with a rotating agitator and evacuated of air.

It is pressurised to 140 kg/cm$^2$ at ambient temperature, and then heated to 180° C. by which the pressure increases to about 200 kg/cm$^2$.

It is kept agitated under these conditions for 40 hours. It is then cooled, depressurised and the reaction mixture filtered from the small amount of insoluble material, and the solution is evaporated under vacuum to give a solid white residue having the following composition:

Al 22.5%
Mg 10.6%
N 17.4%
H$_{act}$ 6.9 meq/g corresponding to the following atomic ratios
Mg/Al=0.52
N/Al=1.5
H$_{act}$/Al=0.83

The yield is 7 g.

On extraction with boiling ethane for 25 hours, the product divides practically in equal parts into the soluble fraction and insoluble fraction. Both the fractions consist of mixed polyimino derivatives of aluminium and magnesium, in accordance with the following compositions:

Insoluble fraction

Al 21.1%
Mg 12.1%
N 18.2% corresponding to the atomic ratios
Mg/Al=0.63
N/Al=1.66

Soluble fraction (solution analysis)

Al=0.163 g. atoms/liter
Mg=0.062 g. atoms/liter
N=0.264 g.atoms/liter corresponding to the atomic ratios
Mg/Al=0.38
N/Al=1.62

Both fractions are amorphous to X-rays, confirming the absence of free poly(N-isopropyliminoalanes), these compounds being notably characterised by high crystallinity.

EXAMPLE 3

A suspension of powdered Mg (120 m moles) and NaAlH$_4$(5 m moles) in a solution of iso-C$_3$H$_7$NH$_2$ (280 m moles) in tetrahydrofuran (300 ml) is fed into a 1 liter stainless steel autoclave provided with an anchor agitator, and previously evacuated of air.

It is pressurized with H$_2$ (140 kg/cm$^2$) at ambient temperature, and then heated to 100° C. by which the pressure increases to about 180 kg/cm$^2$.

It is kept agitated under these conditions for 35 hours, then cooled, depressurized and the reaction mixture withdrawn. This is filtered. (Mg is absent in solution). The insoluble fraction consists of a white powdery product, crystalline to X-rays (the spectrum shows no lines typical of magnesium metal), which is repeatedly washed with tetrahydrofuran to remove the unreacted amine and any aluminium amide derivatives, then dried under vacuum and analysed.

Found values: Mg 16.9%, N 19.4% (the N/Al ratio=2).

Theoretical values for C$_6$H$_{16}$MgN$_2$: Mg 17.3%, N 19.9%.

The I.R. spectrum in nujol shows absorption of the NH group at 3220 cm$^{-1}$.

The yield is 16.6 g.

EXAMPLE 4

A suspension of powdered Mg (100 m moles) and NaAlH$_4$ (5 m moles) in a solution of iso-C$_3$H$_4$NH$_2$ (250 m moles) in toluene (300 ml) is fed into a 1 liter stainless steel autoclave provided with an anchor agitator, and previously evacuated of air.

It is pressurised with H$_2$ (140 kg/cm$^2$) at ambient temperature, and then heated at 200° C. by which the pressure increases to about 210 kg/cm$^2$.

It is kept agitated under those conditions for 40 hours, then cooled, depressurized and the reaction mixture withdrawn.

This is filtered.

The white powdery insoluble product is repeatedly washed with toluene, dried under vacuum and then analysed.

Found values: Mg 17.6%, N 19.5% (the N/Al ratio is 1.92).

Theoretical values for C$_6$H$_{16}$MgN$_2$: Mg 17.3%, N 19.9%.

The X-ray and I.R. spectra show that this is the same product as that of example 1.

The yield is 13.5 g.

EXAMPLE 5

A suspension of powdered Mg (190 m moles) and NaAlH$_4$ (9 m moles) in a solution of iso-C$_3$H$_7$NH$_2$ (170 m moles) in toluene (350 ml) is fed into a 1 liter stainless steel autoclave provided with an anchor agitator and previously evacuated of air.

It is pressurised with H$_2$ (140 kg/cm$^2$) at ambient temperature, and then heated to 180° C. by which the pressure increases to about 200 kg/cm$^2$.

It is kept agitated under these conditions for 35 hours, then cooled, depressurised and the reaction mixture withdrawn. This is filtered.

The solution is evaporated under reduced pressure.

A solid white residue is finally obtained, containing magnesium amide together with small quantities of aluminium amide deriving from the quantity of NaAlH$_4$ used as activator. This latter may be eliminated by hot sublimation under high vacuum. Thus after heating to 160° C. under a vacuum of 10$^{-3}$ mmHg for 6 hours, the residue from evaporating the reaction solution is analysed and consists essentially of magnesium amide with a N/Mg ratio of about 1.5.

Found values: Mg 24.8%, N 21.9%, Al traces. The product is amorphous to X-rays. I.R. analysis shows an absorption which may be attributed to N-H bonds at 3250 cm$^{-1}$. The yield is 9.4 g.

EXAMPLE 6

A suspension of powdered Mg (190 m moles) in a solution of iso-C$_3$H$_7$NH$_2$ (170 m moles) in toluene (350 ml) to which Al(C$_2$H$_5$)$_3$ (8.5 m moles) has been added is fed into a 1 liter stainless steel autoclave provided with an anchor agitator and previously evacuated of air.

It is pressurised with H$_2$ (140 kg/cm$^2$) at ambient temperature, and then heated to 180° C. by which the pressure increases to about 200 kg/cm$^2$.

It is kept agitated under these conditions for 35 hours, then cooled, depressurised and the reaction mixture withdrawn and filtered.

The solution is evaporated under reduced pressure.

The white residue is further dried under vacuum, analysed, and shown to consist of magnesium amide (N/Mg about 1.5) with aluminium amide as impurity.

Found values: Al 3.1%, Mg 22.8%, M 24.6%.

EXAMPLE 7

A suspension of powdered Mg (120 m moles) and NaAlH$_4$ (10 m moles) in a solution of n-C$_4$H$_9$NH$_2$ (300 m moles) in toluene (300 ml) is fed into a 1 liter stainless steel autoclave provided with an anchor agitator and previously evacuated of air.

It is pressurised with H$_2$ (130 kg/cm$^2$) at ambient temperature, and then heated to 200° C. by which the pressure rises to about 200 kg/cm$^2$.

It is kept agitated under these conditions for 48 hours, then allowed to cool, depressurised and the reaction mixture withdrawn This is filtered.

The solution is evaporated under reduced pressure.

A solid white residue is obtained, which, on analysis, is found to consist of a mixture of magnesium amide (N/Mg about 1.5) and aluminium amide in a quantity corresponding to the NaAlN$_4$ used as activator.

Found values: Al 1.8%, Mg 19.5%, N 18.0%. The magnesium amide is amorphous to X-rays. The I.R. spectrum shows a band at 3260 cm$^{-1}$ attributed to N═H bonds.

The yield is 92% relative to the initially fed magnesium.

EXAMPLE 8

A suspension of powdered Mg (125 m moles) and NaAlH$_4$ (5 m moles) in a solution of tertiary butylamine (280 m moles) in toluene (300 ml) is fed into a 1 liter stainless steel autoclave provided with an anchor agitator and previously evacuated of air.

It is pressurised with H$_2$ (130 kg/cm$^2$) at ambient temperature, and then heated to 200° C. by which the pressure rises to about 190 kg/cm$^2$.

It is kept agitated under these conditions for 60 hours, then allowed to cool, depressurised and the reaction mixture withdrawn. This is filtered to separate a clear solution from an insoluble residue.

The concentrated solution is cooled to −5° C. at which crystals separate out, these being then separated by decantation, dried under vacuum and analysed.

Found values: Mg 18.1%, N 17.3%, H$_{act}$ absent.

The atomic N/Mg ratio is 1.66.

The product does not contain aluminium amide impurities.

The I.R. spectrum shows absorption at 3220 cm$^{-1}$ attributable to N-H bonds.

The insoluble fraction from the reaction mixture is repeatedly washed with toluene, dried under vacuum and then analysed.

Found values: Mg 18.5%, N 11%, H$_{act}$ 3.3 meq/g. Aluminium is absent.

EXAMPLE 9

A suspension of powdered Mg (120 m moles) and NaAlH$_4$ (6 m moles) in a solution of piperidine (250 m moles) in toluene (300 ml) is fed into a 1 liter stainless steel autoclave provided with an anchor agitator and previously evacuated of air.

It is pressurised with H$_2$ (140 kg/cm$^2$) at ambient temperature, and then heated to 180° C. by which the pressure rises to about 190 kg/cm$^2$.

It is kept agitated under these conditions for about 12 hours, then allowed to cool, depressurised and the reaction mixture withdrawn.

This is filtered to give a clear solution and an insoluble residue. The solvent is evaporated from the solution to give a solid white product which is analysed.

Found values: Mg 11.1%, N 13.0%. The atomic N/Mg ratio is 2.03.

Calculated values for C$_{10}$H$_{20}$N$_2$Mg: Mg 12.6%, N 14.5%.

The I.R. examination shows no evidence of the presence of free amine, in accordance with the formation of a diamide Mg(N(CH$_2$)$_5$)$_2$.

The yield is 16 g.

EXAMPLES OF POLYMERISATION

EXAMPLE 1

Tetrahydrofuran (50 ml) and methacrylonitrile (10 ml) are fed in that order into a 100 ml flask under a nitrogen atmosphere. The temperature of the solution is raised to 75° C. and (iso-C$_3$H$_7$NH)$_2$Mg (2 m moles) is added under agitation. Polymerisation starts rapidly, indicated by the appearance of a red colouration.

It is kept agitated at 70°–80° C. for 5 hours, then the polymerisation is interrupted with a few ml of methanol and the reaction mixture is poured into an excess of methanol made acid by HCl, to which an antioxidant has been added.

The insoluble polymer is recovered by filtration and dried at 50° C. under vacuum.

The dry polymer yield is 2.8 g. The [η] at 30° C. in dichloroacetic acid is 3.52. The polymer is insoluble to the extent of 94.7% in boiling acetone (the extraction time was 24 h).

EXAMPLE 2

Tetrahydrofuran (50 ml) and methacrylonitrile (10 ml) are fed in that order into a 100 ml flask under a nitrogen atmosphere. The temperature of the solution is raised to 75° C., and magnesium amide (2 m moles) obtained by direct synthesis from Mg and n-butylamine and with a N/Mg ratio of about 1.5 is added under agitation.

Polymerisation commences rapidly. as indicated by the appearance of a red colouration.

It is kept agitated at 70°–80° C. for 5 hours, then the polymerisation reaction is interrupted with a few ml of methanol and the reaction mixture is poured into an excess of methanol made acid with hydrochloric acid to which an antioxidant has been added. The insoluble polymer is recovered by filtration and dried at 50° C. under vacuum.

The dry polymer yield is 4.0 g. The [η] at 30° C. in dichloroacetic acid is 5.53. The polymer is insoluble to the extent of 90% in boiling acetone. (The extraction time was 24 h).

EXAMPLE 3

A methacrylonitrile polymerisation test was carried out using the same method and under the same conditions as example 2, with the difference that the solvent used was benzene. 3.1 g of dry polymer are obtained. The [η] at 30° C. in dichloroacetic acid is 4.57.

The polymer is insoluble to the extent of 94% in boiling acetone. (The extraction time was 24 h).

Example of the preparation of mixed Al and Mg poly-N-isopropyl-iminoalane by the reaction between $Mg(NH-isoC_3H_7)_2$ and $AlH_3 \cdot N(CH_3)$.

Tetrahydrofuran (150 ml) and $Mg(NH-iso\ C_3H_7)_2$ (44 m moles) are fed in that order into a 500 ml flask under a nitrogen atmosphere. A solution of $AlH_3.N(CH_3)_3$ (44 m moles) in tetrahydrofuran (120 ml) is then slowly added under agitation.

$H_2$ is given off. The reaction mixture is kept at the reflux temperature of the solvent for 8 hours.

It is filtered to leave an insoluble residue, and the reaction solution is evaporated under vacuum. A white solid residue (7.5 g) is obtained, which on chemical analysis shows:

Al=15.5%
Mg=7.3%
N=12.0%
$H_{active}$=5.5 mq/g

Calculated values for $[(HAlN-iso-C_3H_7)_2\ (THF-MgN-iso-C_3H_7)]_n$:

Al=16.6%
Mg=7.5%
N=12.9%
$H_{active}$=6.1 meq/g

What we claim is:

1. A process for preparing a magnesium amide consisting of reacting magnesium with a primary or secondary aliphatic amine in the presence of hydrogen having a pressure of about 130 $kg/cm^2$ or greater at ambient temperature, the reaction being carried out at a temperature greater than or equal to about 50° C.

2. A process for preparing a magnesium amide as claimed in claim 1, wherein the reaction is carried out in the presence of an activator wherein the activator is chosen from the metals of the first three groups of the Periodic Table, their hydrides or alkyl derivatives or mixed hydrides thereof, the activator being added to the reaction mixture in a quantity equal to or less than 5 molar % of the reacted amine.

3. A process for preparing a magnesium amide as claimed in claim 1 wherein the reaction is carried out in the presence of a solvent chosen from hydrocarbons or ethers.

* * * * *